US00PP27883P3

(12) United States Plant Patent
Kobayashi

(10) Patent No.: US PP27,883 P3
(45) Date of Patent: Apr. 11, 2017

(54) POINSETTIA PLANT NAMED 'PER1362'

(50) Latin Name: ***Euphorbia pulcherrima* Willd.**
Varietal Denomination: PER1362

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 105 days.

(21) Appl. No.: 14/545,484

(22) Filed: May 12, 2015

(65) Prior Publication Data

US 2016/0338241 P1 Nov. 17, 2016

(51) Int. Cl.
*A01H 5/02* (2006.01)

(52) U.S. Cl.
USPC ..... Plt./303

(58) Field of Classification Search
USPC ..... Plt./263.1, 302, 303
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER1362', characterized by its uniform, upright and mounded plant habit; vigorous growth habit; freely and upright to somewhat outwardly branching habit; dark green-colored leaves; under natural season conditions, plants flower on or about November 8 in Southern California; large inflorescences with peach-colored flower bracts with dark pink-colored flecks and spots; and good post-production longevity.

2 Drawing Sheets

Botanical designation: *Euphorbia pulcherrima* Willd.
Cultivar denomination: 'PER1362'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER1362'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated from a cross-pollination made by the Inventor in December, 2007 of a proprietary selection of *Euphorbia pulcherrima* Willd. identified as code number PE2-31, not patented, as the female, or seed, parent, with *Euphorbia pulcherrima* Willd. 'PER2804', disclosed in U.S. Plant Pat. No. 19,295, as the male, or pollen, parent. The new Poinsettia plant was discovered and selected by the Inventor as a single flowering plant from within the progeny of the stated cross-pollination in a controlled greenhouse environment in Encinitas, Calif. in December, 2008.

Asexual reproduction of the new Poinsettia plant by terminal vegetative cuttings in a controlled greenhouse environment in Encinitas, Calif. since February, 2009 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1362'. These characteristics in combination distinguish 'PER1362' as a new and distinct Poinsettia plant:

1. Uniform, upright and mounded plant habit.
2. Vigorous growth habit.
3. Freely and upright to somewhat outwardly branching habit.
4. Dark green-colored leaves.
5. Under natural season conditions, plants flower on or about November 8 in Southern California.
6. Large inflorescences with peach-colored flower bracts with dark pink-colored flecks and spots.
7. Good post-production longevity.

In side-by-side comparisons conducted in Encinitas, Calif., plants of the new Poinsettia differ primarily from plants of the female parent selection in the following characteristics:

1. Plants of the new Poinsettia have more vigorous than plants of the female parent selection.
2. Plants of the new Poinsettia and the female parent selection differ in leaf and flower bract aspect plants of the female parent selection have leaves and flower bracts that are reflexed.
3. Plants of the new Poinsettia flower about twelve days earlier than plants of the female parent selection when grown under natural season conditions.

In side-by-side comparisons conducted in Encinitas, Calif., plants of the new Poinsettia differ primarily from plants of the male parent, 'PER2804', in the following characteristics:

1. Plants of the new Poinsettia have darker green-colored leaves than plants of 'PER2804'.
2. Plants of the new Poinsettia have smaller flower bracts than plants of 'PER2804'.
3. Plants of the new Poinsettia and 'PER2804' differ in flower bract color as plants of 'PER2804' have bright red-colored flower bracts.

Plants of the new Poinsettia can be compared to plants of the *Euphorbia pulcherrima* Willd. 'Peterstar Pink', disclosed in U.S. Plant Pat. No. 9,879. In side-by-side comparisons conducted in Encinitas, Calif., plants of the new Poinsettia differed primarily from plants of 'Peterstar Pink' in the following characteristics:

1. Plants of the new Poinsettia were more vigorous than plants of 'Peterstar Pink'.
2. Plants of the new Poinsettia had darker green-colored leaves than plants of 'Peterstar Pink'.
3. Plants of the new Poinsettia and 'Peterstar Pink' differed in flower bract color as plants of 'Peterstar Pink' had pink-colored flower bracts.
4. Plants of the new Poinsettia flowered about 17 days earlier than plants of 'Peterstar Pink'.

Plants of the new Poinsettia can be compared to plants of the *Euphorbia pulcherrima* Willd. 'PER975', disclosed in U.S. Plant Pat. No. 16,882. In side-by-side comparisons conducted in Encinitas, Calif., plants of the new Poinsettia differed primarily from plants of 'PER975' in the following characteristics:

1. Plants of the new Poinsettia had darker green-colored leaves than plants of 'PER975'.
2. Plants of the new Poinsettia and 'PER975' differed in flower bract color as plants of 'PER975' had light pink to pale yellow-colored flower bracts.
3. Plants of the new Poinsettia flowered about 13 days earlier than plants of 'PER975'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'PER1362' grown in a container.

The photograph on the second sheet is a close-up view of a typical flowering plant of 'PER1362'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 21 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1362'.

Parentage:

*Female, or seed, parent.*—Proprietary selection of *Euphorbia pulcherrima* Willd. identified as code number PE2-31, not patented.

*Male, or pollen, parent.*—*Euphorbia pulcherrima* Willd. 'PER2804', disclosed in U.S. Plant Pat. No. 19,295.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; white in color.

Plant description:

*Plant habit and form.*—Uniform, upright and mounded plant habit; inverted triangle; large inflorescences positioned above the foliar plane; vigorous growth habit.

*Plant height.*—About 38 cm.

*Plant diameter or spread.*—About 58 cm.

*Lateral branch description.*—Quantity: Freely branching habit, about seven lateral branches develop after pinching; upright to somewhat outwardly branching habit. Length: About 34 cm. Diameter: Thick, about 9 mm. Internode length: About 1.8 cm. Strength: Strong. Aspect: About 45° from vertical. Texture: Smooth, glabrous. Luster: Glossy. Color: More green than 146A.

*Leaf description.*—Arrangement: Alternate, simple. Length: About 13.25 cm. Width: About 10.5 cm. Shape: Ovate with cordate tendencies. Apex: Acuminate. Base: Mostly truncate with cordate tendencies. Margin: Mostly entire, occasionally with broad lobes. Aspect: Flat. Venation pattern: Pinnate, arcuate. Texture, upper and lower surfaces: Smooth, glabrous; slightly rugose. Color: Developing and fully expanded leaves, upper surface: Darker green than N137A or 147A; venation, close to 146A. Developing and fully expanded leaves, lower surface: Close to 147B; venation, close to 146C to 146D. Petioles: Length: About 7.75 cm. Diameter: About 4 mm. Texture, upper and lower surfaces: Smooth, glabrous. Luster, upper and lower surfaces: Glossy. Color, upper surface: Close to 146B. Color, lower surface: Close to 146B to 146C.

Inflorescence description:

*Inflorescence type and habit.*—Terminal inflorescences are compound corymbs of cyathia with colored flower bracts subtending the cyathia; inflorescences uniformly positioned above the foliar plane.

*Fragrance.*—None detected.

*Flowering response.*—Under natural season conditions, plants typically flower on or about November 8 in Southern California; under artificial long nyctoperiod/short photoperiod conditions, plants flower about seven to eight weeks later.

*Post-production longevity.*—Good post-production longevity; plants of the new Poinsettia maintain good substance and flower bract color for about four to six weeks under interior conditions; flower bracts persistent and cyathia not persistent.

*Inflorescence diameter*.—About 35 cm.

*Inflorescence height* (*depth*).—About 5.5 cm.

*Flower bracts*.—Quantity per inflorescence: About 36. Length, largest bracts: About 15 cm. Width, largest bracts: About 11.5 cm. Shape: Ovate. Apex: Acuminate. Base: Obtuse. Margin: Entire, undulate. Texture, upper and lower surfaces: Smooth, glabrous; satiny; somewhat rugose. Aspect: Mostly upright to horizontal. Venation pattern: Pinnate, arcuate. Color: Developing or transitional bracts, upper surface: Ground color, close to 147A; irregular and random sectors, close to 10A and 37B. Developing or transitional bracts, lower surface: Ground color, close to 144A and 146A; irregular and random sectors, close to 10B, 10C, 37A and 37B. Fully expanded bracts, upper surface: Close to 38A and 39C; random flecks and spots, close to 53A; some bracts, close to 38C and 38D with flecks and spots, close to 47A to 47B or 52A; color becoming closer to 22D with late development. Fully expanded bracts, lower surface: Close to 38B and 38C; flecks and spots, close to 53A and 53B; color becoming closer to 16B with late development. Bract petioles: Length: About 4.75 cm. Diameter: About 4 mm. Texture, upper and lower surfaces: Smooth, glabrous. Color, upper and lower surfaces: Close to 144B to 144C.

*Cyathia*.—Quantity per corymb: About 32. Length: About 8 mm. Width: About 6 mm. Shape: Oval. Texture: Smooth, glabrous. Color, inner surface: Close to 144B. Color, outer surface: Close to 144A.

*Nectaries*.—Quantity per cyathium: One. Length: About 7 mm. Width: About 4.5 mm. Shape: Roughly oval. Texture: Smooth, glabrous. Color, inner and outer surfaces: Close to 17C.

*Peduncles*.—Length: About 6 mm. Diameter: About 2 mm. Strength: Strong. Aspect: Mostly upright. Texture: Smooth, glabrous. Color: Close to 144A.

*Reproductive organs*.—Stamens: Quantity per cyathium: About 20. Filament length: About 6 mm. Filament color: Close to 154D. Anther shape: Round; bi-lobed. Anther length: Less than 1 mm. Anther color: Close to 9A. Amount of pollen: None observed. Pistils: Quantity per cyathium: One; triparted. Pistil length: About 6 mm. Stigma shape: Lanceolate, recurved. Stigma color: Close to 53A. Style length: About 5 mm. Style color: Close to 144A. Ovary color: Close to 144A.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1362' as illustrated and described.

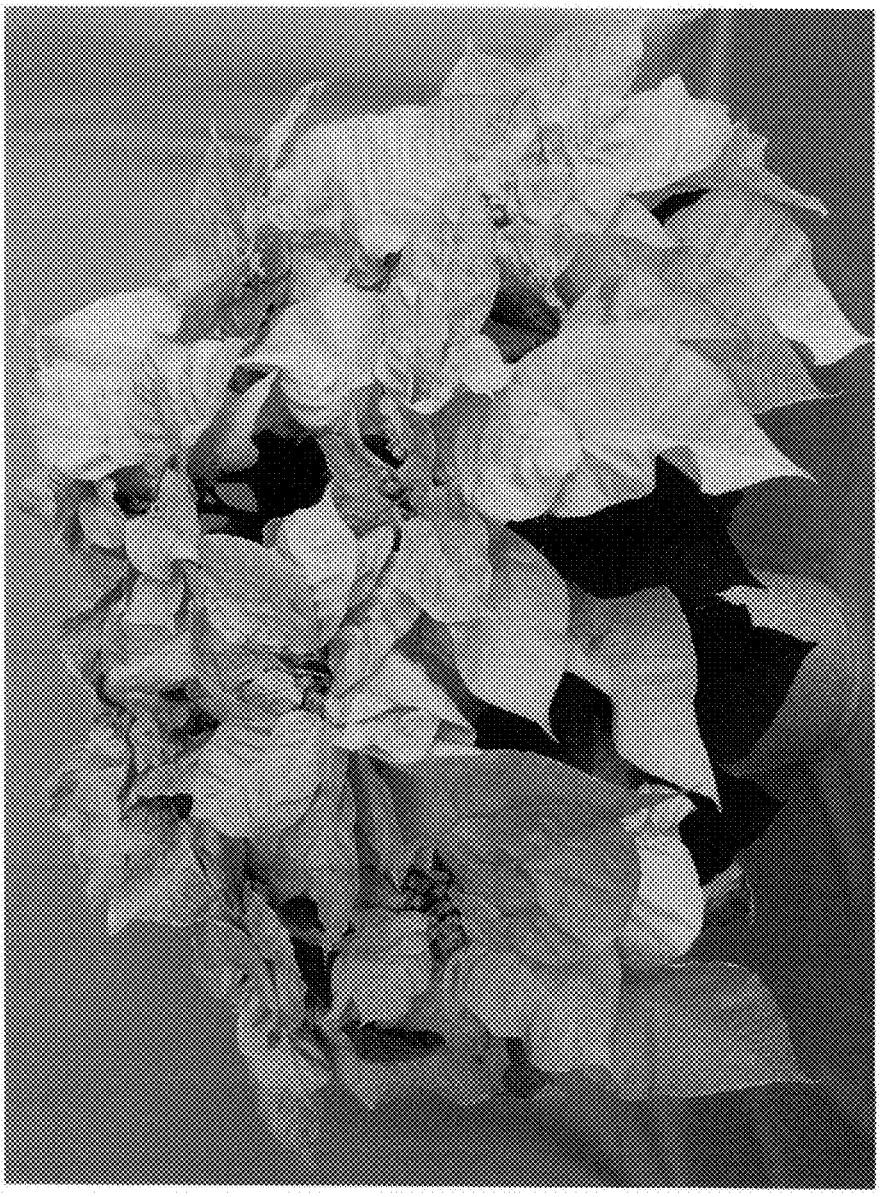

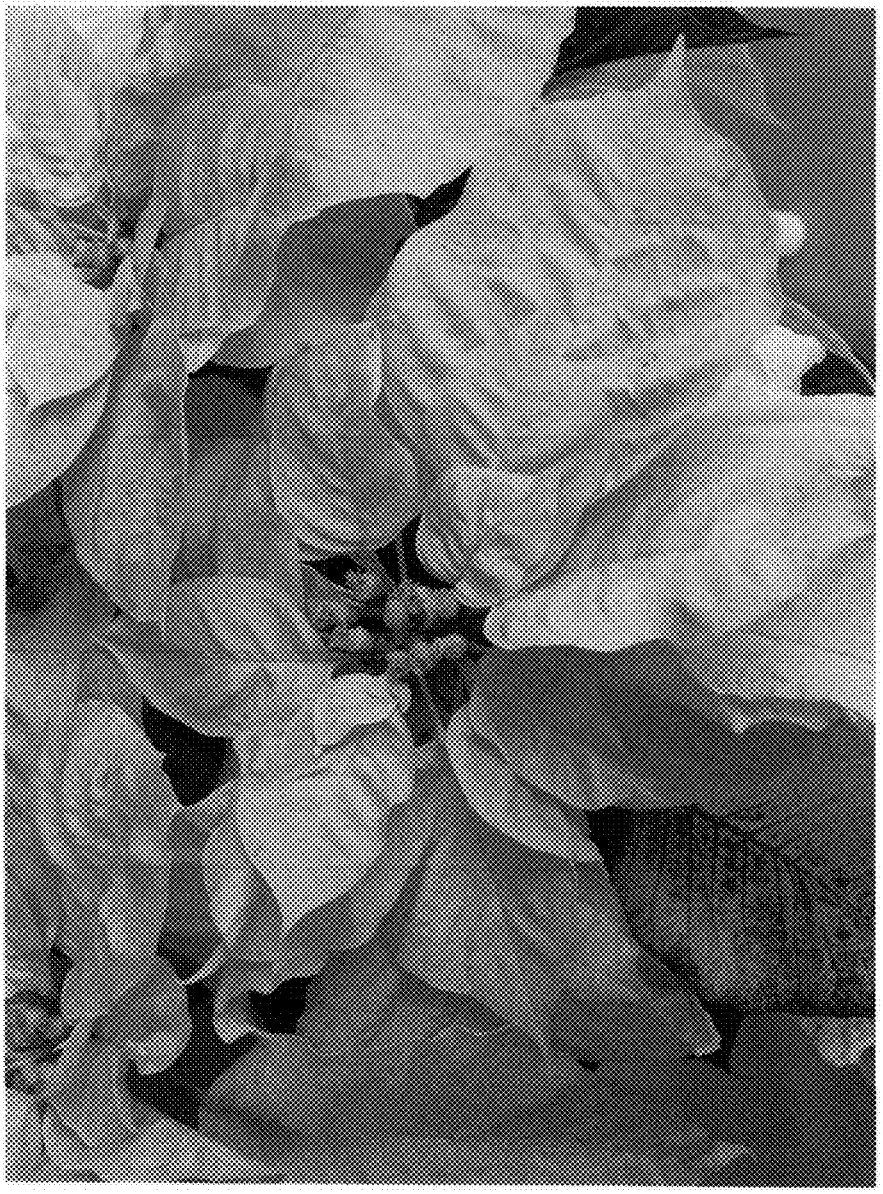

* * * * *